US008288168B2

(12) United States Patent
Morales

(10) Patent No.: US 8,288,168 B2
(45) Date of Patent: Oct. 16, 2012

(54) SIMPLIFIED TISSUE PROCESSING

(75) Inventor: Azorides R. Morales, Coral Gables, FL (US)

(73) Assignee: The University of Miami, Miami, FL (US)

( * ) Notice: Subject to any disclaimer, the term of this patent is extended or adjusted under 35 U.S.C. 154(b) by 1000 days.

(21) Appl. No.: 12/274,613

(22) Filed: Nov. 20, 2008

(65) Prior Publication Data

US 2009/0136992 A1 May 28, 2009

Related U.S. Application Data

(62) Division of application No. 10/971,700, filed on Oct. 25, 2004, now Pat. No. 7,470,401.

(60) Provisional application No. 60/513,560, filed on Oct. 24, 2003.

(51) Int. Cl.
*G01N 1/00* (2006.01)

(52) U.S. Cl. ............. 436/174; 422/63; 422/64; 422/65; 422/50; 422/500; 422/501; 436/180; 427/4; 427/296

(58) Field of Classification Search ............. 422/63–67, 422/50, 500–501; 436/180, 174; 427/4, 427/296
See application file for complete search history.

(56) References Cited

U.S. PATENT DOCUMENTS

| | | |
|---|---|---|
| 2,150,757 A | 3/1939 | Bodine |
| 2,684,925 A | 7/1954 | Ferrari |
| 3,389,052 A | 6/1968 | Ehrenreich et al. |
| 3,546,334 A | 12/1970 | Lerner et al. |
| 3,674,040 A | 7/1972 | Howells et al. |
| 3,892,197 A | 7/1975 | Kinney et al. |
| 3,961,097 A | 6/1976 | Gravlee |
| 3,995,022 A | 11/1976 | Heanley et al. |
| 4,099,483 A | 7/1978 | Henderson |
| 4,141,312 A | 2/1979 | Louder et al. |
| 4,199,558 A | 4/1980 | Henderson |
| 4,221,823 A | 9/1980 | Pearson et al. |
| 4,300,243 A | 11/1981 | Baumgartner |
| 4,545,831 A | 10/1985 | Ornstein |
| 4,578,282 A | 3/1986 | Harrison |
| 4,656,047 A | 4/1987 | Kok et al. |
| 4,670,386 A | 6/1987 | Sugaar |
| 4,681,996 A | 7/1987 | Collins et al. |
| 4,734,260 A | 3/1988 | Lautenschlager |
| 4,784,873 A | 11/1988 | Kienecker et al. |
| 4,835,354 A | 5/1989 | Collins et al. |

(Continued)

FOREIGN PATENT DOCUMENTS

DE 19928820 A1 12/2000

(Continued)

OTHER PUBLICATIONS

Bellotti et al. "Use of the microwave oven for cell block preparation" Acta Cytol. 41:610-611 (1997).

(Continued)

*Primary Examiner* — Jyoti Nagpaul
(74) *Attorney, Agent, or Firm* — Nixon & Vanderhye PC

(57) ABSTRACT

Improved systems and methods for tissue processing are described here. The chemical process and the construction of the apparatus are simplified by using only two different solutions in two separate reaction modules. They are compatible with processing of tissue specimens for genetic analysis, histology, in situ antibody binding and hybridization, archival preservation of morphology and nucleic acids, and combinations thereof.

35 Claims, 3 Drawing Sheets

U.S. PATENT DOCUMENTS

| | | | |
|---|---|---|---|
| 4,839,194 | A | 6/1989 | Malluche et al. |
| 4,857,300 | A | 8/1989 | Maksem |
| 4,882,128 | A | 11/1989 | Hukvari et al. |
| 4,891,239 | A | 1/1990 | Dudley et al. |
| 4,911,915 | A | 3/1990 | Fredenburgh |
| 4,992,763 | A | 2/1991 | Bert et al. |
| 5,023,187 | A | 6/1991 | Koebler et al. |
| 5,030,929 | A | 7/1991 | Moeller |
| 5,049,510 | A | 9/1991 | Repasi et al. |
| 5,068,086 | A | 11/1991 | Sklenak et al. |
| 5,089,288 | A | 2/1992 | Berger |
| 5,104,640 | A | 4/1992 | Stokes |
| 5,122,633 | A | 6/1992 | Moshammer et al. |
| 5,230,865 | A | 7/1993 | Hargett et al. |
| 5,244,787 | A | 9/1993 | Key et al. |
| 5,256,571 | A | 10/1993 | Hurley et al. |
| 5,270,010 | A | 12/1993 | Lautenschlager |
| 5,289,140 | A | 2/1994 | Jorgenson et al. |
| 5,318,795 | A | 6/1994 | Stokes et al. |
| 5,368,820 | A | 11/1994 | Lautenschlager |
| 5,382,414 | A | 1/1995 | Lautenschlager |
| 5,387,397 | A | 2/1995 | Strauss et al. |
| 5,401,625 | A | 3/1995 | Robinson |
| 5,408,074 | A | 4/1995 | Warmbier et al. |
| 5,431,952 | A | 7/1995 | Ocello |
| 5,432,056 | A | 7/1995 | Hartman et al. |
| 5,447,077 | A | 9/1995 | Lautenschlager |
| 5,460,797 | A | 10/1995 | Ryan |
| 5,532,462 | A | 7/1996 | Butwell et al. |
| 5,625,706 | A | 4/1997 | Lee et al. |
| 5,672,696 | A | 9/1997 | Wang et al. |
| 5,679,333 | A | 10/1997 | Dunphy |
| 5,712,605 | A | 1/1998 | Flory et al. |
| 5,725,835 | A | 3/1998 | Lautenschlager |
| 5,750,008 | A | 5/1998 | Lautenschlager |
| 5,767,493 | A | 6/1998 | Lautenschlager |
| 5,782,897 | A | 7/1998 | Carr |
| 5,796,080 | A | 8/1998 | Jennings et al. |
| 5,830,417 | A | 11/1998 | Kingston |
| 5,849,517 | A | 12/1998 | Ryan |
| 5,858,178 | A | 1/1999 | Lautenschlager |
| 5,875,286 | A | 2/1999 | Bernstein et al. |
| 5,976,829 | A | 11/1999 | Birnboim |
| 5,981,924 | A | 11/1999 | Lautenschlager |
| 6,017,725 | A | 1/2000 | Hoffmann et al. |
| 6,033,912 | A | 3/2000 | Lautenschlager |
| 6,042,874 | A | 3/2000 | Visinoni et al. |
| 6,054,695 | A | 4/2000 | Lautenschlager |
| 6,072,086 | A | 6/2000 | James et al. |
| 6,165,723 | A | 12/2000 | Shah et al. |
| 6,183,995 | B1 | 2/2001 | Burmer et al. |
| 6,204,375 | B1 | 3/2001 | Lader |
| 6,207,408 | B1 * | 3/2001 | Essenfeld et al. ............ 435/40.5 |
| 6,242,723 | B1 | 6/2001 | Lautenschlager |
| 6,248,535 | B1 | 6/2001 | Danenberg et al. |
| 6,291,180 | B1 | 9/2001 | Chu |
| 6,303,005 | B1 | 10/2001 | Lautenschlager |
| 6,329,645 | B2 | 12/2001 | Giberson et al. |
| 6,379,921 | B1 | 4/2002 | Pajak |
| 6,455,317 | B1 | 9/2002 | Lautenschlager |
| 6,531,317 | B2 | 3/2003 | Guiguis et al. |
| 6,586,713 | B2 | 7/2003 | Essenfeld et al. |
| 6,717,119 | B2 | 4/2004 | Ondruschka et al. |
| 6,793,890 | B2 | 9/2004 | Morales et al. |
| 6,797,928 | B2 | 9/2004 | Giberson et al. |
| 2001/0000487 | A1 | 4/2001 | Essenfeld et al. |
| 2001/0020599 | A1 | 9/2001 | Lautenschlager |
| 2001/0043884 | A1 | 11/2001 | Essenfeld et al. |
| 2001/0051365 | A1 | 12/2001 | Morales et al. |
| 2002/0084264 | A1 | 7/2002 | Ondruschka et al. |
| 2002/0086346 | A1 | 7/2002 | Ryan |
| 2002/0096340 | A1 | 7/2002 | Ondruschka et al. |
| 2002/0176814 | A1 | 11/2002 | Lautenschlager et al. |
| 2002/0177183 | A1 | 11/2002 | Giberson et al. |
| 2003/0127311 | A1 | 7/2003 | Lautenschlager |
| 2003/0127313 | A1 | 7/2003 | Lautenschlager |
| 2003/0194352 | A1 | 10/2003 | Lautenschlager |
| 2003/0211452 | A1 | 11/2003 | Vincek et al. |
| 2004/0004075 | A1 | 1/2004 | Morales et al. |
| 2004/0043504 | A1 | 3/2004 | Buhler et al. |

FOREIGN PATENT DOCUMENTS

| | | | |
|---|---|---|---|
| EP | 0311035 | A2 | 4/1989 |
| EP | 0311035 | B1 | 4/1989 |
| EP | 0311035 | A3 | 1/1990 |
| EP | 0562877 | A2 | 9/1993 |
| EP | 0680243 | A2 | 4/1995 |
| EP | 0849582 | A2 | 11/1997 |
| EP | 0822403 | A1 | 2/1998 |
| EP | 1455174 | A1 | 9/2004 |
| EP | 1455174 | B1 | 12/2004 |
| GB | 1557722 | | 12/1979 |
| WO | 86/06479 | | 11/1986 |
| WO | 98/05938 | | 2/1998 |
| WO | 99/09390 | | 2/1999 |
| WO | 01/44783 | A1 | 6/2001 |
| WO | 01/44784 | A1 | 6/2001 |
| WO | 2004/033622 | A3 | 6/2001 |

OTHER PUBLICATIONS

Ben-Ezra et al. "Effect of fixation on the amplification of nucleic acids from paraffin-embedded material by the polymerase chain reaction", J. Histochem. Cytochem. 39:351-354 (1991).

Boon et al. "Microwave-stimulated diffusion for fast processing of tissue: Reduced dehydrating, clearing, and impregnating times" Histopathol. 10:303-309 (1986).

Boon et al. "Formaldehyde fixation and microwave irradiation" Histochem. J. 20:313-322 (1988).

Boon et al. "The two-step vacuum-microwave method for histoprocessing" Microwave Newsletter 33:349-358 (1995).

Boon et al. "Microwave irradiation of human brain tissue: Production of microscopic slides within one day" J. Clin. Path. 41:590-593 (1988).

Bostwick et al.,"Establishment of the formalin-free surgical pathology laboratory" Arch. Pathol. Lab. Med. 118:298-302 (1994).

Buesa "Mineral oil: The best xylene substitute for tissue processing yet?" J. Histotechnol. 23:143-149 (2000).

Dimulescu et al. "Characterization of RNA in cytologic samples preserved in a methanol-based collection solution" Mol. Diagnosis 3:67-72 (1998).

Foss et al. "Effects of fixative and fixation time on the extraction and polymerase chain reaction amplification of RNA from paraffin-embedded tissue" Diagn. Mol. Pathol. 3:148-155 (1994).

Frable "Cytology automation" Am. J. Clin. Pathology 101:121-122 (1994).

Gayle et al. "Evaluation of clearing and infiltration mixtures (CIMs) as xylene substitutes for tissue proceesing" J. Histotechnol. 17:137-142 (1994) (abstract only).

Goldsworthy "Effects of fixation on RNA extraction and amplification from laser capture microdissected tissue" Mol. Carcinogenesis 25:86-91 (1999).

Hutchinson "Homogeneous sampling accounts for the increased diagnostic accuracy using the thinprep™ processor" Am. J. Clin. Pathology 101:215-219 (1994).

"Hypercenter™ XP Enclosed Tissue Processor" Shandon pamphlet (1994).

Kok et al. "Major improvement in microscopic-image quality of cryostat sections" Am. J. Clin. Pathol. 88:620-623 (1987).

Kok et al. "Histoprocessing with the microwave oven: An update" Histochem. J. 20:323-328 (1988).

Kok et al. "Microwaves for microscopy" J. Microscopy 158:291-322 (1990).

Kok et al. "Physics of microwave technology in histochemistry" Histochem. J. 22:381-388 (1990).

Kok et al. "Ultrarapid vacuum-microwave histoprocessing" Histochem. J. 27:411-419 (1995).

Koopmans et al. "Optimization of extraction and PCR amplification of RNA extracts from paraffin-embedded tissue in different fixatives" J. Virol. Meth. 43:189-204 (1993).

Kovacs et al. "Experiences with a new vacuum-accelerated microwave histoprocessor" Orv. Hetil. 137:1479-1483 (1996) (English-language abstract only).

Kovacs et al. "Experience with a new vacuum-accelerated microwave histoprocessor" J. Pathol. 180:106-110 (1996).

Leong et al. "Antigen preservation in microwave-irradiated tissues: A comparison with formaldehyde fixation" J. Pathol. 156:275-282 (1988).

Leong et al. "Microwave fixation and rapid processing in a large throughput histopathology laboratory" Pathol. 23:271-273 (1991).

Lewis et al. "Unlocking the archive—Gene expression in paraffin-embedded tissue" J. Pathol. 195:66-71 (2001).

Liotta et al. "Molecular profiling of human cancer" Nature Rev. Genet. 1:48-55 (2000).

Marani et al. "The search for vacuo-microwave technique: The vaccum-microwave oven" Eur. J. Morphol. 34:123-130 (1996).

Maxwell et al. "Use of alcohol fixed cytospins protected by 10% polyethylene glycol in immunocytology external quality assurance" J. Clin. Pathol. 52:141-144 (1999).

"Medite TPC15 Tissue Processor and DUO Tissue Processing System" Mopec pamphlet (1999).

"Microm Tissue Processor HMP 300" Zeiss pamphlet (no date).

"microMED T/T Mega Microwave Labstation for Pathology" Milestone pamphlet (no date).

Moller et al. "Chemical dehydration for rapid paraffin embedding" Biotechnic & Histochemistry 69:289-290 (1994).

Morales (2002) "Comparative usefulness of standard and microwave-assisted tissue processing methods" Histologic 35:40-46.

Morales (2004) "Histopathology while-u-wait?" Bull. Royal Coll. Pathol. 128:19-21.

Morales et al. "Continuous-specimen-flow, high-throughput, 1-hour tissue processing" Arch. Pathol. Lab. Med. 126:583-590 (2002).

Morales et al. "Experience with an automated microwave-assisted rapid tissue processing method" Am. J. Clin. Pathol. 121:528-536 (2004).

"Multiwax Microcrystalline Waxes from Sonneborn" WITCO pamphlet (no date).

"Pathcentre™ Enclosed Tissue Processor" Shandon pamphlet (1995).

"Renaissance Tissue Processor" Ventana Medical Systems pamphlet (2001).

Rohr et al. "A comparison of routine and rapid microwave tissue processing in a surgical pathology laboratory" Am. J. Clin. Pathol. 115:703-708 (2001).

Romaguera et al. "Tools to facilitate and standardize grossing" Histologic 36:17-21 (2003).

Sato et al. "A simplified technique of tissue processing and paraffin embedding with improved preservation of antigens of immunostaining" Am. J. Pathol. 125:431-435 (1986).

Sato et al. "The AMEX method: A multipurpose tissue-processing and paraffin-embedding method. Extraction and purification of RNA and application to slot-blot hydribization analysis" J. Pathol. 163:81-85 (1991).

Slap "New developments in microwave histoprocessing" Am. Biotechnol. Lab. p. 40 (Nov. 2003).

"Sonneborn White Oils" WITCO pamphlet (1987).

Suurmeijer et al. "Notes on the application of microwaves in histopathology" Histochem. J. 22:341-346 (1990).

Takahashi et al. "Freeze substitution and freeze drying for stable, long-term preservation of cytologic specimens for immunostaining" Acta Cytologica 40:396-400 (1996).

"Tissue-Tek V.I.P. Vacuum Infiltration Processor E150/E300 Series" Operating Manual (1992).

"Tissue-Tek V.I.P. Vacuum Infiltration Processor (Bench and Floor Models)" Operating Manual (1992).

"Tissue-Tek WIP Vacuum Infiltration Processor Series" Sakura/Tissue-Tek pamphlet (1996).

Van Dort et al. "Preservation of structure and cytochemical reactivity at the ultrastructural level, using microwave irradiation" Histochem. J. 20:365-372 (1988).

Vincek et al. "A tissue fixative that protects macromolecules (DNA, RNA, and protein) and histomorphology in clinical samples" Lab. Invest. 83:1427-1435 (2003).

Visinoni et al. "Ultra-rapid microwave/variable pressure-induced histoprocessing: Description of a new tissue processor" J. Histotechnol. 21:219-224 (1998).

Zubkova et al. "Acceleration of histologic tissue processing and declacification using a microwave oven" Arkh. Patol. 59:64-66 (1997) (English-language abstract only).

Zubkova et al. "Histologic tissue processing in an automated microwave histoprocessor" Arkh. Patol. 61:48-49 (1999) (English-language abstract only).

* cited by examiner

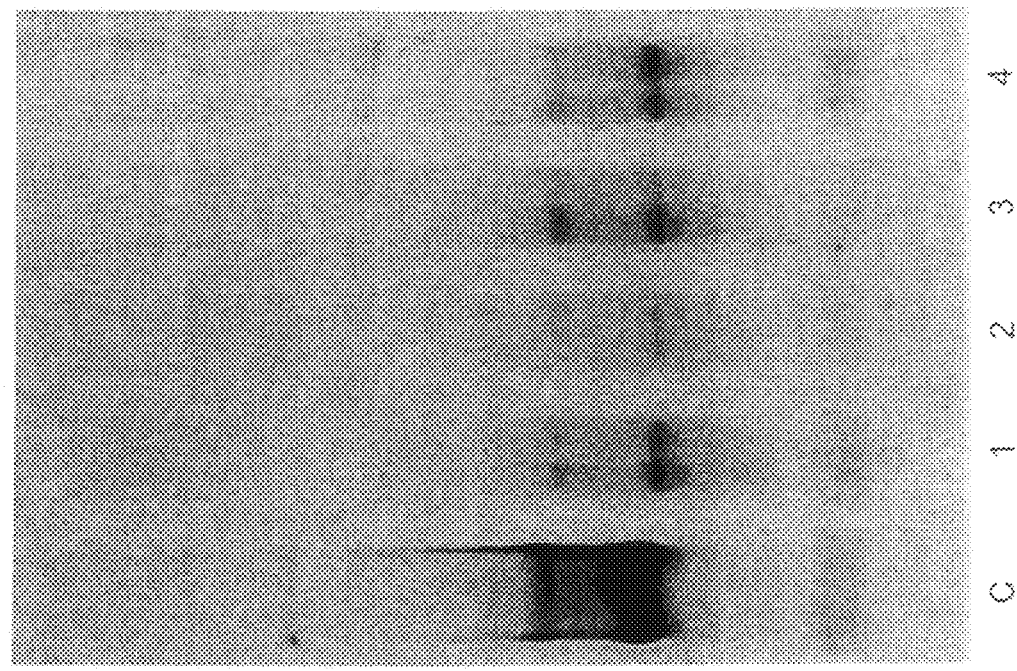

SIMPLIFIED TISSUE PROCESSING

CROSS-REFERENCE TO RELATED APPLICATIONS

This application is a divisional of application Ser. No. 10/971,700, filed Oct. 25, 2004, now U.S. Pat. No. 7,470,401; which claims the benefit of provisional Appln. No. 60/513,560, filed Oct. 24, 2003; all of which are incorporated by reference.

This application is related to U.S. application Ser. No. 09/735,918, filed Dec. 14, 2000, now U.S. Pat. No. 6,793,890 (which claims priority benefit of provisional Appln. No. 60/170,545, filed Dec. 14, 1999); which is a continuation in-part of U.S. application Ser. No. 09/136,292, filed Aug. 19, 1998, now U.S. Pat. No. 6,207,408 (which claims priority benefit of provisional Appln. No. 60/056,102, filed Aug. 20, 1997; all of which are incorporated by reference.

BACKGROUND OF THE INVENTION

1. Field of the Invention

The present invention relates to a chemical process and an apparatus for tissue processing, which are simplified by using only two different solutions in two separate reaction modules.

2. Description of the Related Art

Processes for tissue processing have been described which require use of more than two different solutions, products useful therein, and systems for tissue processing (see WO 99/09390, WO 01/44783, and WO 01/44784). They addressed the need for rapid tissue processing. It is now shown that (i) a non-aqueous admixture and (ii) a wax solution in two separate reaction modules are sufficient to process tissue quickly and completely.

In contrast to the invention disclosed herein, Boon et al. (Eur. J. Morphol. 33:349-358, 1995) use an isopropanol solution and a paraffin wax solution in two separate reaction chambers, each subject to vacuum and microwave heating, to process tissue specimens for histology. Their system requires that tissue specimens be fixed prior to processing and uses a turntable to distribute microwave energy. In addition, the glass container holding the tissue specimens also adsorbs microwave energy and transfers heat to the solution therein.

Milestone (WO 98/05938) provides another alternative for tissue processing in at least three steps: fixing the tissue specimen, simultaneously dehydrating and clearing with dehydrating agent and an essentially lipophilic agent, and impregnating the tissue specimen. Microwave heating is used in the first two steps and elevated pressure is used during the dehydrating/clearing step. The tissue specimen is dried by heating and reduced pressure, and then it is impregnated under vacuum or, alternatively, by applying a cycle of moderate pressure and moderate vacuum.

The cost of automated instruments for tissue processing and expenditures for their operation need to be decreased for efficient delivery of healthcare. Better diagnosis also raises the confidence of patients that their treatment will be based on reliable information and they can be followed by their physicians in a timely manner. A reduction in equipment costs may allow the purchase of additional instruments so they may be distributed across the service area (e.g., primary care facilities). Tissues may be processed locally in such a distributive network and then transported to a specialized pathology facility for analysis. In physician offices and smaller clinics, space is precious and decreasing the size of the automated instrument will allow its placement in a cramped room.

For example, reducing the number of modules in a tissue processing system to two (i.e., one heating module and one vacuum module) will eliminate duplication of mechanical and electrical components and shrink the size of the system. It will be more affordable and easier to place in the laboratory. Fewer chemical compositions will need to be stocked and training personnel in use of the system will be eased.

Processes and systems for tissue processing are now described which use fewer chemical compositions in the former and fewer mechanical and electrical components in the latter as compared to our previously described inventions. This is an improvement over the processes and systems disclosed in U.S. Pat. Nos. 6,207,408 and 6,793,890.

Other advantages of the invention are discussed below or would be apparent to a person skilled in the art from that discussion.

SUMMARY OF THE INVENTION

It is an object of the invention to provide processes and systems for tissue processing which use only two different chemical compositions in the process and minimizes the number of reaction modules in the system.

The system is comprised of (a) one first module in which the reaction contents are at least heated, (b) one second module in which the reaction contents are at least under vacuum and heated, and optionally (c) a conveyance which at least transfers one or more tissue specimens at a time from the first module to the second module. Optional loading and/or unloading stations may also comprise the system.

The first reaction module is comprised of (i) a reaction chamber which is heated and (ii) a non-aqueous admixture. The non-aqueous admixture is comprised of different chemicals with at least three different functions: fixing, dehydrating, and clearing. The reaction chamber of the first module may be comprised of a microwave source with a probe/control circuitry to regulate the microwave energy emanating from the source. Such energy may be used to heat the contents of the reaction chamber to a preset temperature. The module may be further comprised of a heated reservoir to preheat the non-aqueous admixture before transfer to the reaction chamber and to maintain the temperature of the non-aqueous admixture after it is transferred from the reaction chamber. The tissue specimen may be substantially hardened by the chemical composition, microwave radiation, or both; and may be initially impregnated by a liquid hydrocarbon (e.g., mineral oil) and then substantially impregnated by a wax.

The second reaction module is comprised of (i) a reaction chamber which is heated and also connected to a vacuum pump and (ii) a wax solution. The reaction chamber of the second module may be comprised of control circuitry and appropriate probes to regulate the temperature and pressure therein. The module may be further comprised of a reservoir. In the optional reservoir of the second module, solid wax may be melted therein and then maintained as a solution until it is transferred to the reaction chamber.

Alternatively, the system is comprised of a single module in which the reaction contents are successively at least heated and then are at least under vacuum and heated. One or more tissue specimens remain in the same reaction chamber during processing. A non-aqueous solution and a wax solution are successively transferred from two separate reservoirs into the reaction chamber. An optional conveyance may be used to transfer the tissue specimens from optional loading and/or unloading stations.

Further aspects and advantages of the invention will be apparent to a person skilled in the art from the following detailed description and claims, and generalizations thereto.

BRIEF DESCRIPTION OF THE DRAWINGS

FIG. 2 shows the 18S and 28S rRNA bands after separation by denaturing gel electrophoresis. RNA extracted from fresh mouse liver was used as the positive control (lane C). RNA was extracted from processed liver tissue of two mice (lanes 1 and 2 from the first mouse; lanes 3 and 4 from the second mouse). Lanes 1 and 3 were processed for 15 minutes in each reaction; lanes 2 and 4 were processed for 30 minutes in each reaction.

DESCRIPTION OF SPECIFIC EMBODIMENTS OF THE INVENTION

Figure 1A:
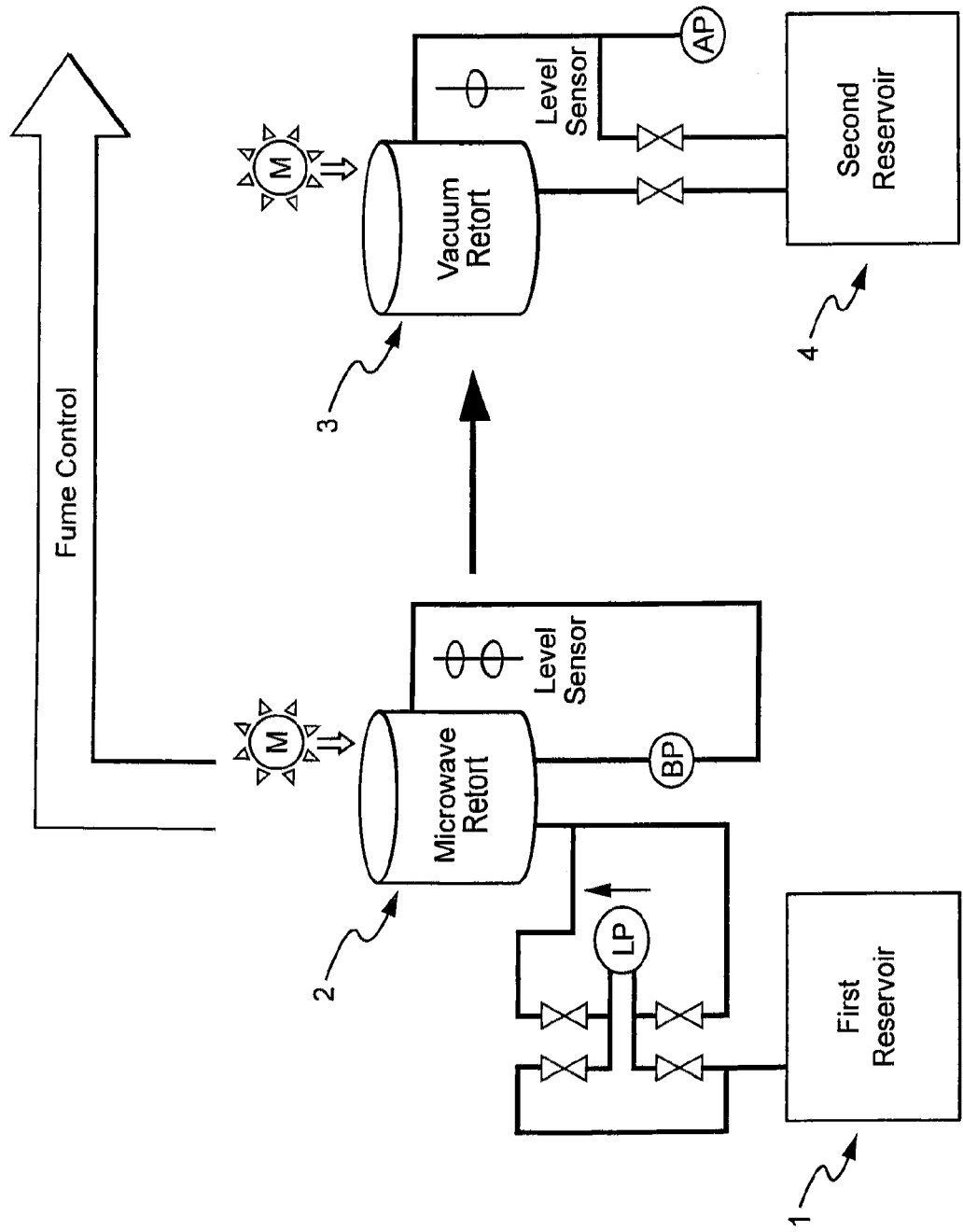
FIG. 1A is a schematic of one embodiment of the invention. A non-aqueous admixture is stored in a first reservoir 1 and is transferred to a microwave retort 2 to contact the tissue specimens. Tissue specimens are then transferred from microwave retort 2 to vacuum retort 3. A wax solution is stored in a second reservoir 4 and is transferred to a vacuum retort 3 to contact the tissue specimens.

With regard to the processing and analysis of solid tissue, a tissue slice must be on the order of 3 to 6 microns to be examined under a microscope, whereas the thinnest slice of fresh tissue that can be obtained by cutting is about 1 mm with the typical slice being on the order of about 2-3 mm. In order to produce a sufficiently thin slice for microscopic examination, it is necessary to harden the tissue so that a thinner slice can be obtained (e.g., by sectioning with a microtome).

In the present invention, the number of (a) different chemical compositions and (b) mechanical and electrical components of the system required for tissue processing has been decreased as compared to the prior art. The system is comprised of a single first reaction module in which the reaction contents are at least heated (e.g., a heating unit); a single second reaction module in which the reaction contents are at least under vacuum (e.g., a vacuum unit); and (iii) a conveyance which at least transfers one or more tissue specimens at a time from the first module to the second module. Each module is comprised of a reaction chamber and a chemical composition which is optionally contained within the reaction chamber.

Chemical compositions are typically transferred between a module's reaction chamber and its optional reservoir which are in fluid communication with each other (e.g., tubing or piping, valves, and pumps with control circuitry to determine the timing, speed, and direction of flow for a chemical composition). One or more tissue specimens may be substantially hardened and initially impregnated in the first module, and then the substantially hardened tissue specimens are impregnated with wax and embedded in a block which is capable of being sectioned. Agitation (e.g., aeration, cycles of vacuum and increased pressure, shaking, etc.) may be used to accelerate exchange between tissue specimen and chemical composition. Successful completion of tissue processing is indicated by the ease and quality of sectioning during microtomy and histologic examination of the sections.

Tissue specimens are hardened with a non-aqueous admixture of chemicals. A suitable admixture is a non-aqueous solution comprised of fixing, dehydrating, and clearing functions (e.g., at least two or three different chemicals). Exemplary agents with fixing and/or dehydrating functions are ketones, alcohols, or a combination thereof. For a non-aqueous admixture of fixative and dehydrant, the volume ratio of the two agents may be between about 1:10 to about 10:1 (although such extremes may change the processing time or results may be less reliable); greater than about 1:6, about 1:3, or about 1:2; less than about 2:1, about 3:1, or about 6:1; about 1:1, or any intermediate range thereof (e.g., between about 1:1 to about 6:1). Clearing function may be provided by an aliphatic hydrocarbon, benzene, limonene, mineral oil, toluene, and xylenes; mineral oil is a preferred clearant because it is nonflammable and nonvolatile. The tissue specimen may be incubated for at least about 2 minutes, at least about 5 minutes, at least about 10 minutes, at least about 15 minutes, at least about 30 minutes, at least about 45 minutes, or at least about 60 minutes. The temperature of incubation may be between about 30° C. and about 80° C.; greater than about 40° C., about 50° C., about 55° C., or about 60° C.; less than about 70° C. or about 75° C.; or any intermediate range thereof (e.g., between about 55° C. and 75° C.).

A tissue specimen which has been hardened may then be impregnated with a wax solution. Consistent with dehydration of the tissue specimen, the wax solution is preferably as low as possible in water content. Thus, the wax solution may be prepared prior to impregnation by heating the wax to evaporate any dissolved water and by degassing under reduced pressure. Impregnation of the tissue specimen may take place under less than atmospheric pressure and at elevated temperature to remove any solvents from the tissue specimen and to draw the wax solution into the tissue specimen. Vacuum decreases impregnation time by accelerating diffusion and reducing the evaporation temperature of any solvents that may be present in the specimen. The wax solution may comprise paraffin and/or other waxes, which has been degassed and dehydrated. The tissue specimen may be incubated for at least about 3 to about 10 minutes, at least about 15 minutes, at least about 30 minutes, at least about 45 minutes, or at least about 60 minutes. The wax solution may be a solid at room temperature (e.g., below about 25° C. or about 30° C.) and molten above about 55° C. or about 60° C. The temperature of incubation may be between about 50° C. and about 90° C., greater than about 55° C. or about 60° C.; less than about 75° C., about 80° C., or about 85° C.; or any intermediate range thereof (e.g., between about 55° C. and 85° C.). It is preferred that the incubation be conducted under reduced pressure (e.g., about 100 torr or below about 760 torr). Prior to sectioning, the impregnated tissue specimen may be embedded in the impregnating agent to form a tissue block.

The reaction chamber may be comprised of any combination of the following: a closure adapted to fit the reaction chamber and to isolate the reaction chamber from the operator's surroundings (e.g., a lid attached or removable from the reaction chamber); thermal insulation to retain heat in the reaction chamber; at least one temperature and/or pressure probe to monitor conditions in the reaction chamber; a seal to isolate electronic components from chemicals in the reaction chamber; and control circuitry which receives input from at least one probe and/or timer. Similarly, a heated reservoir may be comprised of any combination of thermal insulation, at least one temperature and/or pressure probe, a seal, and control circuitry which receives input from at least one probe and/or timer. A rubber gasket is preferred for the reaction chamber (as well as optional heated reservoir) of the first module to isolate fumes of the non-aqueous admixture from the operator. For the second module, a vacuum seal is preferred for the reaction chamber.

In a preferred embodiment, the non-aqueous admixture is premixed and stored in a bottle prior to use. The bottle is opened and at least some of its contents drawn into a first reservoir to be preheated. Solid wax is melted in a second reservoir, and then the wax solution is drawn into the reaction chamber of the second module. The non-aqueous admixture is transferred between reservoir and reaction chamber of the first module during tissue processing; in contrast, the wax solution is maintained in the reaction chamber of the second module during tissue processing. At the end of the day, the non-aqueous admixture is drawn back into the bottle, the wax solution is drawn back into the second reservoir, and the solutions are safely disposed or stored for reuse.

Alternatively, a single reaction chamber may be used within a module which combines both heating and vacuum functions in a single unit. In succession, the non-aqueous admixture and the wax solution are transferred from separate first and second reservoirs, respectively, to the reaction chamber and back again.

Such system may be manually operated or automated (i.e., transfer of tissue specimen between modules with a mechanical conveyance). An automated system may be further comprised of a loading and/or unloading station. Tissue specimens may be loaded into the system and processed either in batches or as separate specimens. Tissue specimens may enter the system at the loading station and exit the system from the unloading station where they are optionally collected. Control circuitry (e.g., hardware and software) may be used to program the movement of tissue specimen(s) in the system, to prevent access to the reaction modules during operation, to modify reaction parameters (e.g., time, temperature, pressure, or amounts of chemicals of the process), or any combination thereof.

Here, a "tissue specimen" is a piece of tissue that may be processed by the methods disclosed herein. It may also refer to single cells from any biological fluid (e.g., ascites, blood, pleural exudate), or cell suspensions obtained from aspiration of solid organs or lavage of body cavities. Single cells may be pelleted by buoyant centrifugation or sedimentation prior to processing. Solid pieces (i.e., tissue slices) are commonly processed for histology and pathology.

Fixing function may be provided by ketones (e.g., acetone, methyl ethyl ketone); aldehydes (e.g., acetaldehyde, formaldehyde, glutaraidehyde, glyoxal); low-molecular weight alcohols (e.g., methanol, isopropanol, ethanol, propanol, butanol, isobutanol, ethyl butanol, amyl alcohol); or the like. Fixative in the non-aqueous admixture may be greater than about 15% (v/v), 20% (v/v), about 25% (v/v), about 30% (v/v), about 35% (v/v), or about 40% (v/v); less than about 35% (v/v), about 40% (v/v), about 45% (v/v), about 50% (v/v), about 55% (v/v), about 60% (v/v), or about 65% (v/v); or any intermediate range thereof (e.g., between about 20% and 60%). Dehydrating function may be provided by low-molecular weight alcohols (e.g., methanol, isopropanol, ethanol, propanol, butanol, isobutanol, ethyl butanol, amyl alcohol); ketones (e.g., acetone, methyl ethyl ketone); or the like. Dehydrant in the non-aqueous admixture may be greater than about 15% (v/v), 20% (v/v), about 25% (v/v), about 30% (v/v), about 35% (v/v), or about 40% (v/v); less than about 35% (v/v), about 40% (v/v), about 45% (v/v), about 50% (v/v), about 55% (v/v), about 60% (v/v), or about 65% (v/v); or any intermediate range thereof (e.g., between about 20% and 60%). In contrast to conventional fixation with aldehydes (e.g., formalin), use of ketones and alcohols is believed to act as fixatives by physically stabilizing proteins (e.g., precipitation) without chemically combining with them. Aliphatic hydrocarbons, benzene, limonene, mineral oil, toluene, and xylenes may be used for their clearing function; mineral oil is preferred. Clearant may be greater than about 10% or about 15% (v/v) of the non-aqueous admixture; it may be less than about 25% or about 30% (v/v) of the non-aqueous admixture. Processing may be accelerated by addition of a surfactant: e.g., dimethyl sulfoxide (DMSO), polyoxyethylene sorbitan esters (e.g., TWEEN 80), sodium dimethyl sulfosuccinate, mild household detergents, or the like. The non-aqueous admixture may also be buffered with the appropriate use of acid and base.

Microwave radiation may also assist hardening of the tissue in a physical rather than chemical manner. The combination of physical and chemical processes may decrease processing time and/or increase specimen quality. The effect of a particular physical or chemical treatment can be determined by noting the effect on tissue processing of omitting the treatment.

Finally, the tissue specimen is impregnated with an agent such as wax (e.g., paraffin), mineral oil, or non-water-soluble waxes. Preferred impregnating agents are commercial wax formulae, mixtures of waxes of different melting points (waxes are solid at room temperature and have melting points which are dependent on their chain lengths, while mineral oil is liquid at room temperature), and the like.

The tissue specimen may be fresh, partially fixed (e.g., fixation in 10% formalin for 2-3 hours), or fixed (e.g., overnight fixation in 10% formalin or any other fixative). The above process allows processing of a tissue specimen from fixation to impregnation in less than about two hours, less than about 90 minutes, less than about 60 minutes, less than about 30 minutes, or less than about 15 minutes. The time required for solution in each step to reach the appropriate temperature is insignificant compared to incubation time for each step, and may be disregarded to calculate the total time for processing. In particular, small biopsies and tissues less than about 1.5 mm thick, as well as those containing little or no fat, could be processed quickly. Tissue may be transported from the operating room to the pathology laboratory in a non-aqueous admixture as disclosed in published U.S. Appln. 2003/0211452: UM-FIX as used here is about 10% low molecular weight, polyethylene glycol (PEG) and about 90% methanol. This preservative was also characterized in Vincek et al. (Lab. Invest. 83:1-9, 2003). With the exception of PEG that is present from tissue preserved in UM-FIX and which is carried into the process of the present invention, PEG is not used and does not appear to be required for tissue processing. This simplifies the chemistry of the present invention and reduces the number of incubations which are necessary in comparison to the previous process.

Following impregnation, the tissue specimen can be embedded to produce a block. The agent used to embed the tissue specimen is preferably the same as the material used for impregnation, but a different impregnating agent may also be used. The blocked tissue specimen can be mounted on a microtome to produce tissue sections of between about 1 micron and about 50 microns, or between about 2 microns and about 10 microns. Tissue sections may be further processed for histochemical staining, antibody binding, in situ nucleic acid hybridization or amplification, or a combination thereof. The tissue specimens are then typically examined by microscopy, but other techniques for detecting cellular properties may be used to examine the processed tissue specimen (e.g., automated cytometry, autoradiography, electrophoresis of nucleic acid). Tissue blocks may be stored for archival purposes or retrospective studies.

Cell phenotypes (e.g., reactivity with cell-specific antibody, chemical staining) may be analyzed by removing the embedding material (e.g., deparaffinization) and dissecting tissues (e.g., proteolytic digestion and mechanical disaggregation). Single cells may be dispersed in a spray and analyzed in a flow cytometer. Alternatively, deparaffinized tissue may be mounted on a microscope stage, dissected with a laser and/or micromanipulator into substantially homogeneous cell populations, and the different cell types analyzed by physical, chemical, or genetic techniques.

The present invention is compatible with preparation of nucleic acids, DNA or RNA, from processed tissues. Thus, genetic study is possible for specimens collected routinely in the clinical pathology laboratory. The combined power of these technologies will be great, Histological observations may be correlated with genetics by analyzing one section by staining or immunohistochemistry, and preparing nucleic acids from an adjacent section for genetic analysis. For example, diseased and normal regions of the same section may be compared to detect genetic differences (e.g., mutations, levels of transcription), disease progression may be characterized by comparing genetics differences in samples taken at several time points, and tumor evolution may be assessed by following the accumulation of genetic differences from primary cancer to metastasis. Substantially homogeneous or merely enriched cells may be obtained by sorting with a flow cytometer or microdissection.

Mutations may be germline and used to trace genetic predisposition of disease, or mutations may be somatic and used to determine genetic alterations in disease pathogenesis. The disease may be a metabolic or neurologic disorder, malignancy, developmental defect, or caused by an infectious agent. The present invention preserves material for genetic analysis by a simple procedure and room temperature storage. It may be analyzed by in situ hybridization or nucleic acids may be extracted from tissue.

Hematoxylin-eosin staining is commonly used for histological study and may be considered a standard for comparison by pathologists. In addition, the present invention may be compatible with other stains including trichrome, reticulin, mucicarmine, and elastic stains as described in general references such as Thompson (*Selected Histochemical and Histopathological Methods*, C. C. Thomas, Springfield, Ill., 1966), Sheehan and Hrapchak (*Theory and Practice of Histotechnology*, C. V. Mosby, St. Louis, Mo., 1973), and Bancroft and Stevens (*Theory and Practice of Histological Techniques*, Churchill Livingstone, New York, N.Y., 1982). Such staining procedures would take between 30 minutes and several hours to complete, although rapid staining procedures are available from Fisher Scientific that require only five minutes to accomplish.

Tissue may be obtained from an autopsy, a biopsy (e.g., endoscopic biopsy), or from surgery. Small specimens such as punch or needle biopsies obtained with a trochar are well suited for the present invention. For cancer surgery, the ability to provide a pathological diagnosis from a stained tissue section will provide the surgeon with information that may be used prior to the patient's departure from the operating room. For example, an indication from the pathologist that the cancer is confined to the resected tissue may allow the surgeon to be conservative in treatment and to preserve neighboring healthy tissue. Alternatively, a finding by the pathologist that cancer is not confined to a resected organ would permit more aggressive surgical treatment while the patient was still in the operating room. In contrast to conventional histological processing of frozen tissue, the processing of fresh tissue in accordance with the invention may provide tissue specimens with better morphology and reduce the need for later confirmation by a pathologist viewing fixed tissue.

Exemplary tissues which may be processed in accordance with the invention include: appendix, bladder, bone, bowel, brain, breast, carcinoma, cervix (squamous epithelium), gall bladder, heart, kidney, liver, lung, ovary, parotid gland, placenta, prostate, skin, spleen, testicle, thyroid gland, tonsil, and uterus (myometrium and endometrium). Lymphoreticular and fatty tissues may be processed in accordance with the invention. Mineralized tissue would require decalcification prior to processing by the present process. Subsequent analysis would include detecting DNA mutations and RNA expression, genomics, histology, immunochemistry, and proteomics.

Tissue sections processed by the present process may also be used in immunohistochemistry. The present process provides tissue specimens in which antigen is recovered and preserved, the choice of fixative may be optimized for recovery and preservation of particular antigens. Non-specific binding sites are blocked, antigen is bound by specific antibody (i.e., the primary antibody), and non-bound antibody is removed. If labeled with a probe or signal generating moiety, the primary antibody may be detected directly but it is preferred to attach the probe to a protein (e.g., a secondary antibody) that specifically binds the primary antibody. Secondary antibody may be raised against the heavy or light chain constant region of the primary antibody. This amplifies the signal generated by an antigen-antibody conjugate because each primary antibody will bind many secondary antibodies. Alternatively, amplification may occur through other specific interactions such as biotin-streptavidin. Antibody binding is performed in a small volume to reduce usage of expensive reagents and maintain a high binding rate; evaporation of this small volume is reduced by incubation in a humidity chamber. The signal generating moiety is preferably an enzyme which is not otherwise present in the tissue. For example, alkaline phosphatase and horseradish peroxidase may be attached to the secondary antibody or conjugated to streptavidin. Substrates are available for these enzymes that generate a chromogenic, fluorescent, or luminescent product that can be detected visually.

The staining pattern for antigen may be used to localize expression of the antigen in the context of cellular structures revealed by counterstaining. Antigen expression can identify cell or tissue type, developmental stage, tumor prognostic markers, degenerative metabolic processes, or infection by a pathogen.

Antigen-antibody binding may also be visualized with fluorescent, radioactive, or colloidal metal probes by epifluorescence, autoradiography, or electron microscopy. Similar probes may be used to detect nucleic acid in the tissue section by in situ hybridization to identify genetic mutations or transcripts; alternatively, the nucleic acid (DNA or RNA) may be extracted from tissue sections and analyzed directly by blotting, or amplified prior to further genetic analysis.

Tissue processing may be integrated with other automated systems: e.g., an embedding and sectioning system which produces a block of paraffin-embedded tissue; a microtomy, staining, and coverslipping system which provides slides containing tissue sections; a developing system which visualizes histochemical and/or immunochemical signals on the tissue sections; a flow cytometer which analyzes and/or sorts single cells by their phenotypes into substantially homogeneous or merely enriched populations; a microdissection system which separates tissues into substantially homogeneous populations; an imaging system which scans tissue sections on a slide, digitizes signals visualized through a microscope, and then manipulates, stores, and transmits those images; and combinations thereof. Cells or tissues, especially those sorted and/or separated into substantially homogeneous populations, may be further analyzed by their DNA or RNA sequences, genetic mutations, changes in the level or pattern of gene expression, changes in the level or pattern of protein expression, and combinations thereof. System integration and data management is facilitated by identifying tissue specimens or their holders by alphanumeric characters, bar code, radiofrequency identification (RFID), or other labeling. The same or different labels may be used to identify a particular tissue specimen as it proceeds through a series of automated systems. The labels and other information about the specimen (e.g., patient name, date, location in the facility, disease or other pathological condition, tissue type, diagnosis, phenotype, genotype, genomic or proteomic characterization) may be entered into a database management system to store, manipulate, and retrieve the data. Mining such information in the database may prove or disprove correlations in accordance with statistical criteria, and suggest further investigations.

An initial step in the process, which may be carried out in the surgical theater, pathology laboratory, or elsewhere, is to prepare a suitable tissue specimen for hardening and, ultimately, examination. Typically, a slice of the tissue of interest is prepared. A fine slice or trochar sample may be obtained for processing: about 0.5 mm to about 1 mm thick, about 1 mm to about 3 mm thick, about 1 mm to about 2.5 mm thick, or about 1.5 mm to about 2 mm thick. The tissue slice is placed in a tissue cassette or other holder in which the tissue is contained during subsequent processing until the hardened specimen is ready for sectioning. Alternatively, a tissue specimen is prepared by coring or snipping tissue with a trochar (e.g., for biopsy). For ease of handling many cassettes, the cassettes may be placed in a carrier or basket. The cassette or holder is next placed in a non-aqueous admixture in accordance with the present invention.

A tissue cassette or holder is exposed to the non-aqueous admixture which hardens tissue while simultaneously being agitated and subjected to microwave radiation. A single microwave unit is needed because only one hardening solution is needed. The hardening solution may remain in the reaction chamber through several cycles of tissue processing or it may be transferred between the reaction chamber and a storage chamber at intervals (e.g., removed to storage chamber after every cycle of hardening, when all tissue specimens have been processed, or at the end of operations during the day). A carrier of tissue specimens or cassettes containing a solid tissue specimen may be transferred between reaction chambers manually, or by an armature or track conveyance.

To provide for agitation which accelerates tissue processing, aeration is provided. A tube may be inserted directly into the non-aqueous admixture below the tissue specimens, but for more uniform and complete agitation, a diffusion plate at the bottom of the reaction chamber and across a substantial portion of its diameter may be used for uniform agitation of the entire volume of solution. Agitation may also be provided by pressure and vacuum (P/V) cycles (e.g., periods of about 10 to 30 seconds spent under pressure, reduced to a partial vacuum, and under pressure again) or pumping solution into and out of the receptacle (e.g., circulating the solution through the receptacle) or using P/V cycles.

The tissue cassette or holder is placed in a wax solution contained in a vacuum unit. Conventionally, wax is degassed as a part of the tissue processing procedure. Degassing removes organic solvents and excess moisture from the wax. To enhance this process and to reuse the wax in the system, continuous degassing under vacuum may be performed.

Next, the tissue specimen is embedded (preferably with an automated embedder). The embedded tissue specimen is then sectioned with a microtome and floated on water for placement on a glass microscope slide (preferably with an automated sectioner). After the section is placed on the slide, the slide is heated to melt the paraffin and adhere the sections to the glass. The slides are then stained (preferably with an automated stainer) and covered (preferably with an automated coverslipper).

In a preferred embodiment, the system for hardening and impregnating a tissue specimen in accordance with the present invention can be limited to two discrete modules: a microwave unit and a vacuum unit. The tissue specimen is contacted with the non-aqueous admixture which hardens fixed or unfixed tissue in the microwave unit. Impregnation of the hardened tissue specimen is finished in the vacuum unit. Only one vacuum unit is required for impregnation. Agitation may be provided with a mechanical device that causes aeration in, shaking or vibration of, or transfer of ultrasound energy into the solution. Alternatively, a pump may be used for agitation using P/V cycles or circulating the solution.

A microwave unit of the invention is comprised of (i) a source of the microwave energy (e.g., magnetron, klystron, traveling wave tube), (ii) a waveguide that transmits the microwave energy from the source to a reaction chamber, its dimensions and shape being adapted for this purpose, and (iii) a reaction chamber that receives the transmitted microwave energy and is adapted to process a tissue specimen by at least chemical fixation, dehydration, and defatting. The reaction chamber may contain a plurality of different tissue specimens. Preferably, the interior geometry of the reaction chamber is configured to achieve uniform distribution of microwave energy and heating of its contents. Uniformity is achieved primarily by consideration of two factors.

First, the circumference of the reaction chamber is made to be an integral number of half wavelengths of the microwave radiation in the chamber. With proper arrangement of the waveguide entrance into the reaction chamber, a mode will be excited that will propagate around the exterior wall. This type of mode is characterized by the microwave field being predominantly near the exterior wall. A similar phenomenon occurs in acoustics where sound waves travel very efficiently next to solid walls. These types of modes are referred to as whispering gallery modes.

A second consideration is the radial distance between the boundary of solution in the reaction chamber and its wall. The optimum spacing is determined empirically by changing that spacing. If the spacing is too narrow, the microwave radiation is absorbed primarily near the waveguide entrance to the reaction chamber. If the spacing is too wide, the reaction chamber becomes a resonant cavity and is sensitive to the amount of non-aqueous admixture and solids (e.g., tissue specimens, cassettes, and basket) therein. With the proper spacing, efficient heating of the solution and solids is achieved over an extensive range of heights of the contents as measured by a level sensor outside the reaction chamber (i.e., volumes therein). As little as 10% of the full height (i.e., total volume) still provides efficient heating of the contents.

Similarly, the source and the waveguide are configured to achieve minimal energy loss during transmission of the microwave radiation. The microwave unit is configured with a waveguide to have no more than about 2% energy loss from the source to the reaction chamber. A higher energy loss would require the use of expensive shielding and other protection devices for the source of the microwave energy.

Heating may be controlled by cycling power on-off in cycles of about 10 to 25 seconds because a minimum time is required by the heating characteristics of the cathode of the microwave source. But this may burn the tissue, so heating may be controlled through a variable current source to allow continuous variation in the power delivered by the microwave source to the reaction chamber. Such burning or over cooking is typified by homogeneous staining of tissue structures without distinguishing cellular features. The latter is preferred to reduce peak power output.

The microwave unit may be further comprised of any combination of a container adapted to fit in the reaction chamber and to receive at least one tissue specimen (e.g., a basket); at least one temperature and/or pressure probe to monitor conditions in the reaction chamber; one or more energy probes to monitor microwave energy being sent by the source, transmitted through the waveguide, and/or received by the reaction chamber; a closure adapted to fit the reaction chamber and to isolate the reaction chamber from the operator's surroundings; thermal insulation to retain heat in the reaction chamber; shielding to isolate electronic components from chemicals in the reaction chamber; and control circuitry to receive input from at least one probe or timer and thereby regulate at least one of the microwave energy from the source, transmitted through the waveguide, and/or received in the reaction chamber. The container is preferably transparent to microwave radiation and therefore energy is not consumed in its heating.

Characteristics of the materials used for the vacuum seal are the ability to hermetically isolate reaction chamber or reservoir from the environment, optionally substantial transparency to microwave radiation, malleability to ensure a tight fit which conforms to the closure, and chemical resistance to solutions of the process. Modifying a reaction chamber or reservoir with (i) a closure and a gasket/seal to reduce evaporation and (ii) thermal insulation can reduce the power required to operate the heater or vacuum unit by two- or three-fold.

The modules may occupy the same space and/or the tissue specimen may remain stationary. Microwave or thermal energy may be regulated and transmitted into the same space, or onto the stationary tissue specimen at different times in the process. Chemical solutions and/or vapors may be moved into or out of the same space, or brought into or out of contact with the stationary tissue specimen. Preferred is minimizing space requirements for the system by using two reaction chambers, and transporting the different chemical compositions into a reaction chamber by tubing or piping from separate storage and/or waste chambers. A controller can receive input from the reaction chamber and/or from timing that part of the processing cycle, and thereby regulate the transport of the different chemical compositions.

Either transferring different solutions into and out of the reaction chamber or transferring the basket among reaction chambers containing different solutions may effect changes in reaction steps. Holding the basket above the interior of the reaction chamber for about 5 to 10 seconds allows excess solution to drain back through one or more openings in the bottom and/or sides before the basket is transferred. Thus, the sequence in which the basket is transferred among reaction chambers, each containing a particular composition of tissue processing chemicals, and the time the basket is incubated in each reaction chamber will dictate the series of chemical reactions necessary to accomplish the process according to the invention.

The lid can be removed; the gasket can be attached to the lid and moved with it. This process of removing the lid and gasket is performed for both the reaction chamber which initially contains the tissue specimens and the next reaction chamber into which the tissue specimens will be subsequently transferred. The basket is then removed, allows solution to drain from the basket and any cassettes which may be contained therein back into the reaction chamber for about 5 to 10 seconds, and transfers the basket to the reaction chamber containing the next chemical solution in the process. Flushing of the tubing/piping and cleaning of the reaction chamber are not required because the amount of solution left behind is minimal. Finally, the lids and gaskets are replaced. The total time for such a transfer is about one minute.

In accordance with the invention, variations on the above embodiments are envisioned. Various configurations of the tissue processing system are possible, and optional modules may be connected to form a portion of the system. The specific configuration chosen may be dictated by the average number of specimens that will be processed on a daily basis by the clinical laboratory, and/or the speed with which histology or pathology reports must be prepared.

The system may be manually operated or automated. Manual operation is particularly suited for research and development because variations in the process or apparatus may be quickly assessed, or in facilities processing a small number of specimens. For automated instruments, tissue specimens may be transported by a mechanical conveyance (e.g., robot arm, track formed by belt and roller) and/or chemical compositions may be transferred by corrosion-resistant plumbing. Thus, tissue processing may be automated by transferring specimens between stationary modules in a particular sequence, filling and emptying modules of different chemicals such that stationary tissue specimens are incubated in a particular sequence, or any combination thereof. Programs which control parameters of tissue processing (e.g., startup and shutdown of instrument, loading and unloading a number of specimens, conditions such as reaction time, progress of specimens through the system) may be monitored on a screen; parameters of tissue processing (e.g., specimen in reaction chamber for about 15, 30 or 45 minutes) may be preset or selected by the operator through a keypad.

The armature conveyance may, for example, grab the specimen with a pincer-like mechanism or catch the specimen with a hook-like device. The arm may be articulated to perform human-like motion; or may be mounted in a fixed coordinate rack with linear or two dimensional movement, and optionally another dimension of movement provided by varying the height of the arm over the system. The track conveyance may be made from resilient or tacky material to fix the specimen on the track by friction, or there may be a regular series of bumps or walls to trap the specimen therebetween. The track may be formed as a continuous belt or may be a series of belts that convey the tissue specimen, with the belt put into motion with a roller or sprocket mechanism. The cassette or holder may be adapted for conveyance by having a stem (with or without a knob) to be grabbed or a loop to be caught by the arm, or by fitting within a groove or indentation in the track. Similarly, the cassette or holder may be organized in a carrier or basket for processing a large number of specimens, the carrier or basket being adapted for transport by the armature or track conveyance.

Electric motors and controllers may be used to transport a tissue specimen by the operator's real-time command or selection of a stored program. A simple mechanism of controlling the time spent by the tissue specimen in each module would be to move the tissue sample or holder thereof at a constant speed and to adjust the length of the path through each module to accommodate the intended incubation time.

The flexible tubing or fixed piping, as well as other components of the plumbing, should be made of chemical-resistant materials to prevent corrosion (e.g., glass, stainless steel, polyethylene, polytetrafluoroethylene, polyvinylchloride). Controllers and pumps/valves may be used to transport chemical compositions from storage chamber to reaction chamber, from reaction chamber to storage chamber if the composition can be reused, and from reaction chamber to waste chamber if the composition is to be flushed from the system; to fill the storage chamber; and to flush the waste chamber by the operator's real-time command or selection of a stored program. A heated reservoir and heated plumbing components may be necessary to maintain the chemical composition at reaction temperature or to ensure that the chemical composition (e.g., wax solution) is kept in a transportable fluid state. Vapor seals and/or cooling may be necessary to isolate corrosive vapors from the mechanical and electrical components of the system.

All of the patents, patent applications, and other publications cited in this specification are incorporated herein by reference in their entirety.

The following examples are meant to be illustrative of the present invention, but the practice of the invention is not limited or restricted in any way by them.

EXAMPLES

Example 1

Tissue processing with a series of non-aqueous solutions is described in U.S. Pat. No. 6,207,408. In particular, a series of four solutions was used to successfully process tissue for histological examination in PCT publication WO 01/447683 and published U.S. Appln. 2001/0051365. Experience using this prior invention has been described by Morales et al. (Arch. Pathol. Lab. Med. 126:583-590, 2002; Am. J. Clin. Pathol. 121:528-536, 2004). Here, we modified the program used in a rapid tissue processor with a series of four solutions in separate modules to determine the contribution of each solution to successful microtomy and histology. Using these modifications, different solutions in the four modules of the system were selected and the results are summarized in Table 1. The requirement for each solution was assessed with a variety of formalin-fixed tissues which were about 1.5 mm thick.

TABLE 1

Only two solutions are required for successful tissue processing

| Microwave Unit | | Vacuum Unit | | | |
|---|---|---|---|---|---|
| I | II | III | IV | Microtomy | Histology |
| 15 min | 15 min | 15 min | 15 min | +++ | +++ |
| 30 min | | 15 min | 15 min | + | + |
| 45 min | | 15 min | 15 min | + | ++ |
| | 45 min | 15 min | 15 min | ++ | +++ |
| | 45 min | 45 min | | − | − |
| | | 45 min | 45 min | ++ | ++ |
| | | 60 min | 60 min | +++ | +++ |

Solution I: 40% isopropanol, 40% acetone, 20% polyethylene glycol (MW 300), glacial acetic acid added to a concentration of about 0.5% total volume, and dimethyl sulfoxide (DMSO) added to a concentration of about 1% total volume at about 62° C.
Solution II: 55% isopropanol, 25% acetone, 20% mineral oil, glacial acetic acid added to a concentration of about 0.5% total volume, and dimethyl sulfoxide (DMSO) added to a concentration of about 1% total volume at about 62° C.
Solution III: 30% mineral oil and 70% molten paraffin at about 65° C. and a pressure of about 640 torr.
Solution IV: molten paraffin at about 65° C. and a pressure of about 640 torr.

In a modification of the tissue processing described in Example 4 of WO 01/447683 and published U.S. Appln. 2001/0051365, specimens were processed in a tissue processor under variable control. The initial process used four modules (i.e., two microwave units and two vacuum units with four different solutions each) and incubation times of 15 minutes per module. Programming the tissue processor to extend incubation times and to skip modules using solutions I and III demonstrated that both the four solution/one hour process and the two solution/two hour process produced excellent results (+++). To be considered excellent, microtomy of tissue blocks had to produce acceptable ribbons of serial sections which could be floated in a water bath without "exploding" and then positioned on a glass slide for histological staining without "cracking" consistently and uniformly through a variety of tissue types. This handling characteristic of tissue sections after cutting with a microtome was essential to provide efficient and reliable pathological diagnoses based upon the morphology observed in stained sections. Portions of the section which were missing or poorly stained would prevent rendering an opinion on the morphology of the tissue in that section and thereby reduce confidence in diagnostic conclusions. Therefore, procedures and instruments which are used in a clinical pathology laboratory require validation that they can be consistently and efficiently performed, a variety of tissue types can be processed and different diagnostic criteria can be applied to processed tissues using a standardized protocol, and precious specimens will be reliably processed. Both processes produce excellent results. But the present invention has the advantage of requiring only two different chemical compositions and half the number of system components required for tissue processing using a series of non-aqueous solutions. The longer processing time is an acceptable compromise and may be mitigated by use of thinner tissue specimens and/or preprocessing of specimens.

During microtomy, poorly processed tissue specimens do not form a ribbon of serial sections, the section explodes when floated in a water bath, and there are cracks (i.e., missing portion) in the section. "Good" and "excellent" tissue processing results do not suffer from such defects because microtomy produces sections with preserved morphology (e.g., cellular structure and tissue organization) during subsequent analysis (e.g., histological staining, antigen binding by antibody, in situ hybridization). But good (++) results are variable: (a) inconsistent with sections from the same tissue type or (b) consistent with some tissue types but unsatisfactory with other tissue types. Such variable results are not acceptable for diagnostic purposes because it is preferable to use the same protocol for all specimens processed in the laboratory.

Elimination of solution II did not produce excellent results even when the time of incubation for solution I was lengthened to 45 minutes. Microtomy showed that paraffin sections floated on a water bath would unacceptable spread out on the surface and "explode" prior to placement on glass slides. Histology, however, showed that there were fewer "cracks" after hematoxylin-eosin staining of deparaffinized sections when incubation in solution I was lengthened from 30 minutes to 45 minutes.

Therefore, the remaining investigations were performed with solution II and without solution I. Incubation in solution II was 45 minutes or 60 minutes. Processing with 15 minutes each in solutions III and IV did not produce sections with acceptable handling characteristics. Serial sections did not produce acceptable ribbons although the histology was adequate. Use of only solution III was disastrous (cf. only solution III for 45 minutes to only solution IV for 45 minutes) because the blocks could not be sectioned. The combination of only solutions II and IV produced at least good results in regards to microtomy and histology. But incubation times of 60 minutes instead of 45 minutes are preferred because the former could process both fresh and formalin-fixed specimens while the latter did not acceptably process fresh tissue. The shorter incubation time also gave inconsistent results with "cracks" in lymphoreticular tissues (e.g., spleen) and unacceptable morphology with fatty tissues (e.g., breast). Diverse tissue types have been successfully processed with the longer incubation time (see below).

Example 2

Fresh, formalin-fixed, and UM-FIX-treated tissue specimens of about 1.0 mm to about 2.0 mm (preferably about 1.5 mm) in the thinnest dimension have been processed, Bladder, breast, carcinoma of the lung, cervix (squamous epithelium), kidney, liver, ovary, spleen, tonsil, and uterus (endometrium and myometrium) gave uniformly excellent results for microtomy and histology (hematoxylin-eosin staining of deparaffinized sections).

The non-aqueous admixture is comprised of:
about 25% acetone
about 55% isopropanol
about 20% mineral oil
glacial acetic acid added to a concentration of about 0.5% total volume DMSO added to a concentration of about 1% total volume. The three major components were mixed in a volume of 3.8 L, and then the acetic acid and DMSO were added. Specimens were incubated for about 60 minutes in this non-aqueous admixture at about 62° C.; chemical exchange was promoted by agitating the non-aqueous admixture (e.g., aeration). Both the specimen and the non-aqueous admixture were heated by microwave energy during incubation.

Following hardening of the tissue specimen by chemicals in the non-aqueous admixture and/or microwave irradiation, the tissue specimen was impregnated for 60 minutes in molten paraffin, which was degassed and dehydrated, at about 65° C. and a reduced pressure of about 640 mm of Hg. Impregnation was promoted by agitating the wax solution with P/V cycles. After a total processing time of about two hours, the tissue specimen was ready for microtomy and subsequent analysis, or storage.

For thicker tissue specimens (e.g., about 2.5 mm thick slice), the incubation times with non-aqueous admixture and wax solution may have to be lengthened to about 90 minutes or 120 minutes for each solution.

Example 3

Fresh, formalin-fixed, and UM-FIX-treated tissue specimens of about 1.0 mm to about 2.0 mm (preferably about 1.5 mm) in the thinnest dimension have been processed. Uniformly excellent results for microtomy and histology (hematoxylin-eosin staining of deparaffinized sections) have been obtained for human tissues (e.g., adenoid, breast, kidney, lipoma, liver, placenta, skin, spleen, and uterus) under the following conditions (i.e., two reactions each for about 30 minutes).

The non-aqueous admixture is comprised of:
about 50% acetone
about 30% isopropanol
about 20% mineral oil
glacial acetic acid added to a concentration of about 0.5% total volume DMSO added to a concentration of about 1% total volume. The three major components were mixed in a volume of 3.8 L, and then the acetic acid and DMSO were added. Specimens were incubated for about 30 minutes in this non-aqueous admixture at about 62° C.; chemical exchange was promoted by agitating the non-aqueous admixture (e.g., aeration). Both the specimen and the non-aqueous admixture were heated by microwave energy during incubation.

Following hardening of the tissue specimen by chemicals in the non-aqueous admixture and/or microwave irradiation, the tissue specimen was impregnated for 30 minutes in molten paraffin, which was degassed and dehydrated, at about 65° C. and a reduced pressure of about 640 mm of Hg. Impregnation was promoted by agitating the wax solution with P/V cycles. After a total processing time of about two hours, the tissue specimen was ready for microtomy and subsequent analysis, or storage.

For smaller biopsy specimens obtained with a trochar (e.g., a cylinder of about 2 mm to about 3 mm in diameter), the incubation times with non-aqueous admixture and wax solution may have to be shortened to about 15 minutes for each solution.

In other embodiments, appendix, bowel, breast, fallopian tube, kidney, liver, lung, parotid, placenta, prostate, thyroid, and uterus have been processed for microtomy and histology when each reaction time was shortened to about 20 minutes. In yet other embodiments, adenoma, appendix, breast, cervix, gall bladder, kidney, liver, lung, ovary, skin, spleen, thyroid, tonsil, and uterine body (as well as fresh mouse liver) have been processed for microtomy and histology when each reaction time was shortened to about 15 minutes.

Example 4

Tissue processing may be performed using an embodiment of the invention (shown in FIG. 1A) in the following manner. A bottle of a non-aqueous admixture (3.8 L) is attached and paraffin pellets (3 L) are added. The non-aqueous admixture is prewarmed and the solid paraffin, which had been degassed and dehydrated when in liquid form, is melted prior to loading of samples. Vacuum is drawn and air pressure is raised to transfer solutions and, if needed, provide agitation of solutions within the retort by bubbling (pump BP) or P/V cycling (pump AP). A connection (e.g., flexible tubing) and a port where the connection joins different components of the system may be used to transfer solution between a first reservoir and microwave retort using a pump LP and solenoid valves. Only impregnation in the vacuum retort requires a reduction in the pressure with an air pump because tissue processing in the microwave retort (e.g., hardening and initial impregnation) is performed at atmospheric pressure with mechanical agitation using a bubbling pump.

Solutions and retorts are warmed to appropriate operating temperatures. For example, the non-aqueous admixture is preheated to about 55° C. by an electric heater in the reservoir of the first module (first reservoir 1) prior to transfer into the microwave retort 2. The non-aqueous admixture is typically transferred back to the first reservoir 1 prior to opening the microwave retort 2 so that tissue specimens are placed in an empty reaction chamber. Similarly solid paraffin is melted in the reservoir of the second module (second reservoir 4) from which the wax solution is typically transferred to the vacuum retort 3 at the start of daily operation and returned to the second reservoir 4 at the end of the day. The temperature of the solution is maintained at about 62° C. in the microwave retort 2 and at about 65° C. in the vacuum retort 3. Tubing between (i) first reservoir 1 and microwave retort 2 or (ii) second reservoir 4 and vacuum retort 3 provide two-way fluid communication. The two reservoirs 1 and 4 for non-aqueous and wax solutions are separate. The presence or absence of solution and/or basket in a retort 2 or 3 may be determined with a level sensor to detect the volume or displacement of the solution.

A perforated basket containing tissue specimens in cassettes is loaded. A loading station is optional so the basket may be placed in a reaction chamber of the loading station (if present) which contains non-aqueous admixture, on a conveyance which transfers a basket to the microwave retort 2 (and subsequently to the vacuum retort 3), or directly into the reaction chamber of the microwave retort 2. The conveyance is preferably a robot arm with a hook which reversibly attaches to the basket; a pan with a replaceable absorbent liner is attached to the robot arm and swivels under the basket to catch dripping non-aqueous admixture or wax solution. A lid is attached to each reaction chamber by a hinge; each lid forms a seal with the reaction chamber using a rubber gasket, and is opened/closed by a chain driven with an electric motor M. Finally, when tissue impregnation is complete, the loaded basket is transferred from the vacuum retort 3. An unloading station is optional and a reaction chamber of the unloading station (if present) is empty so that excess molten paraffin can drain from the basket. The time required to transfer the basket between stations is less than about 10 seconds. The tissue cassettes can then be unloaded from the basket.

The process described in Example 2 or 3 may be used in this system. A non-aqueous admixture is transferred between microwave retort 2 and heated reservoir 1. The basket is transferred into an empty reaction chamber of microwave retort 2, the lid of the reaction chamber is closed, non-aqueous admixture is transferred into the microwave retort 2 from the heated first reservoir 1 to contact tissue specimens, non-aqueous admixture is returned to the heated first reservoir 1 when incubation is complete (i.e., tissue specimens are suitably hardened), the lid is opened and the basket is transferred to the vacuum retort 3 containing wax solution, and tissue specimens are incubated therein until impregnation is completed.

The reaction chamber containing an impregnation agent is heated using a radiant heating source. Alternatively, a heater maintains the temperature of water circulating in tubing in contact with the impregnation agent to keep it in a molten state. For example, a coil of tubing can be located inside the reaction chamber; this heating coil would then transfer heat to the contents. Preferably the heating coil is eliminated by wrapping the outside wall of the reaction chamber with electrical wire that conducts heat through the walls into the contents of the reaction chamber. Agitation in the vacuum retort can be performed by P/V cycles of nominal pressure 0.35 Kg/cm$^2$ and 500 mm Hg vacuum.

Other conditions (e.g., times and temperatures of each incubation) are as described in Examples 2-3. The system may be enclosed in a cabinet to contain any fumes which may be present and to vent them (fume control). A tabletop system may use a mechanical conveyance to transfer tissue specimens or they may be manually transferred. Alternatively, a door with a glass window at torso height allows the operator to access the system when there is no movement of the basket, to load a basket in or to unload a basket from the system, and to observe movement of the basket. For safety, it is preferred that the door locks when the arm or lid on a retort is moving. Another door at knee height allows the operator (i) to attach a bottle of the non-aqueous admixture to a port leading to the first reservoir 1 which is connected to the microwave retort 2 and (ii) to melt paraffin in the second reservoir 4 which is connected to the vacuum retort 3.

Figure 1B:
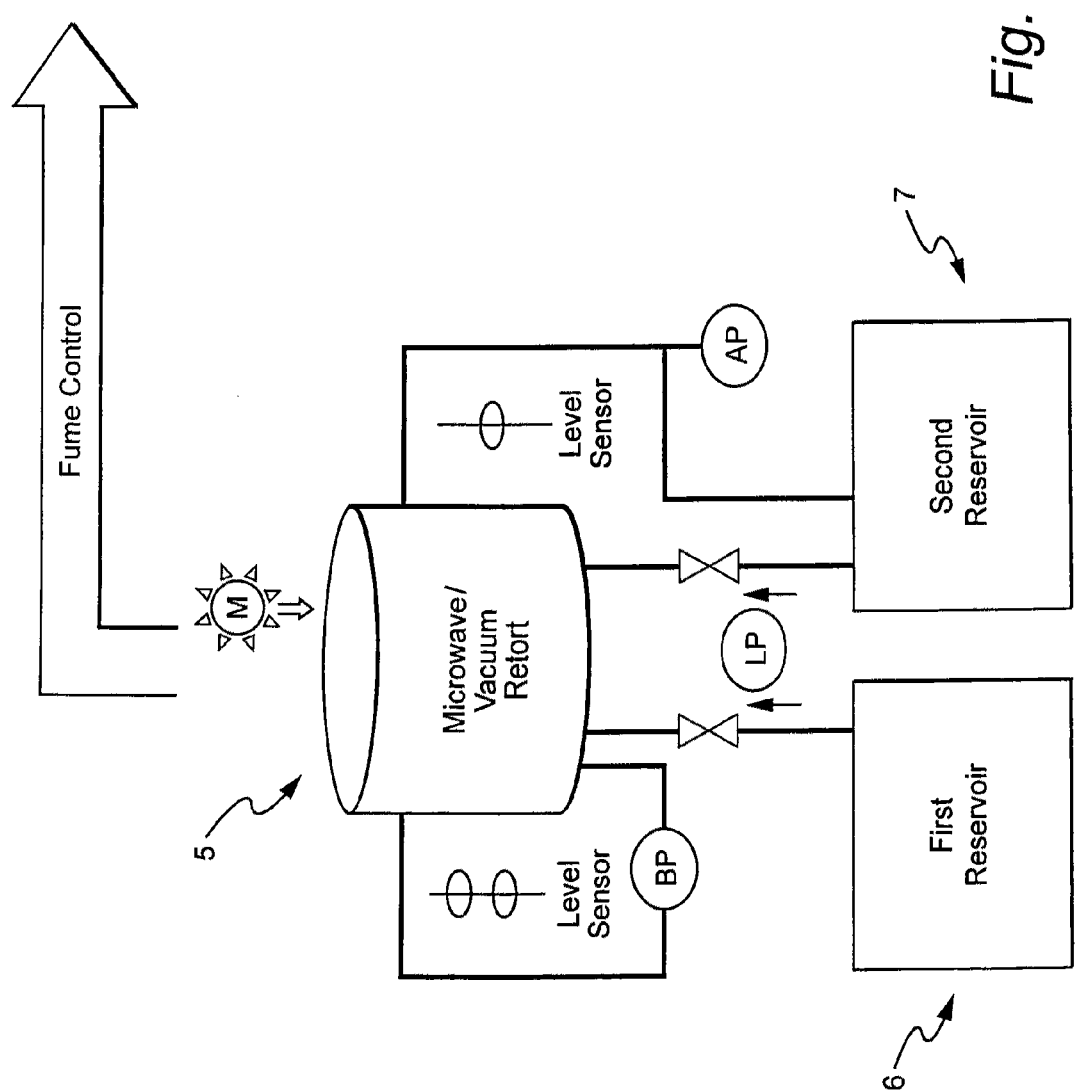
FIG. 1B is a schematic of an alternative embodiment of the invention. Tissue specimens are processed in a microwave/vacuum retort 5. A non-aqueous admixture is stored in a first reservoir 6 and a wax solution is stored in a second reservoir 7. The non-aqueous admixture and then the wax solution are transferred to microwave/vacuum retort 5 to contact the tissue specimens.

In an alternative embodiment (FIG. 1B), a single retort 5 may be used with both microwave and vacuum functions combined in the same location. A non-aqueous admixture from a first reservoir 6 and a wax solution from a second reservoir 7 are successively transferred into the microwave/vacuum retort 5 to eliminate having to transfer tissue specimens between two retorts.

Example 5

Detection of Antigen in Tissue Sections

Tissue specimens were fixed in formalin or UM-FIX, and then processed for 30 minutes in each of the two reactions. Paraffin sections were cut on a microtome to a thickness of 3 microns, placed in a water bath, and floated onto a glass slide. Paraffin was melted by placing slides in either a 58° C. oven for 30 minutes, or preferably in a 37° C. oven for approximately 18 hours or overnight, and then dewaxed in a xylene bath for 10 minutes. Slides were rehydrated in decreasing ethanol solutions for one minute each (two baths of absolute alcohol, two baths of 95% alcohol, and one bath of 90% alcohol), and then rinsed by submerging in tap water for 2 minutes.

Endogenous peroxidase was blocked with a solution of 6% hydrogen peroxide ($H_2O_2$) and methanol, or 35 ml of 6% $H_2O_2$ with 140 ml of methanol, incubated for 15 minutes. Slides were rinsed by submerging in tap water for 2 minutes and phosphate buffered saline (PBS) for 2 minutes, then dried.

Slides were transferred to a humidity chamber and normal horse serum (NHS) was added to block for 10 minutes. Excess normal horse serum was decanted from slides, and specific primary antibody was incubated for 30 minutes on the tissue section in a humidity chamber at room temperature. Slides were flushed with PBS with a back-and-forth motion using a squeeze bottle, submerged in a PBS bath for 2 minutes, and excess PBS was dried off each slide. Linking solution (also known as secondary antibody or biotinylated anti-rabbit or anti-mouse) was added to each tissue section and incubated for 25 minutes in a humidity chamber at room temperature. Such rabbit, rat, and mouse secondary antibodies (e.g., anti-IgM, anti-IgG) may be obtained from Dako (Carpinteria, Calif.) and used at a dilution of about 1:600. Slides were flushed with PBS using a squeeze bottle, submerged in a PBS bath for 2 minutes, and excess PBS is dried off each slide.

Signal was developed according to the manufacturer's instructions (Vector Laboratories). Avidin-biotin complex (ABC) solution was added to the tissue section and incubated for 25 minutes in humidity chamber. Slides were flushed with PBS in a squeeze bottle and submerged in a rack in a PBS bath for 2 minutes. The rack was submerged in a bath of diaminobenzidine (DAB) chromogen for 6 minutes, then submerged under running water to wash gently for 4 minutes. Tissue sections were counterstained with hematoxylin (staining time will depend on the age of the hematoxylin) from about 15 seconds to 90 seconds at room temperature. Slides were washed under running water for 3 minutes to remove excess counterstain, dehydrated in alcohol baths (about 10 seconds in each) from 85% alcohol to absolute alcohol, cleaned in xylene, and coverslipped. Results are shown in Table 2.

TABLE 2

Antibody staining of tissue sections (m., monoclonal; p, polyclonal)

| Tissue | Fixative | Antibody | Staining | Comments |
|---|---|---|---|---|
| Prostate | Formalin | cytokeratin HMK (m M630, Dako) | + | staining confined to benign glands, focus of adenocarcinoma is negative |
|  |  | AMACR (p 5045, Dako) | − |  |
| Tonsil | Formalin | CD20 (m M755, Dako) | + | pattern of reactivity as expected |
|  |  | CD10 (m NCL-DC10-270 Vector) | + |  |
|  |  | CD3 (p A0452, Dako) | + |  |
| Liver | Formalin | HepPar 1 (m M7158, Dako) | + | staining confined to hepatocytes |
|  |  | cytokeratin 7 (m M7018, Dako) | + | selective staining of bile duct epithelium |
| Lung | UM-FIX | thyroid transcription factor-1 (m M3575, Dako) | +/− | positive in pneumocytes; negative in adenocarcinoma |
|  |  | P63 (m P09-OP09L, Oncogene Science) | +/− | positive in basal bronchial epithelium; tumor negative |
| Breast | Formalin | CD31 (m M823, Dako) | + | endothelium |
| Kidney | Formalin | renal cell antigen (m NCL-RCC, Vector) | + |  |
|  |  | glomerular epithelial protein (m BioGenex) | + |  |
| Lung | UM-FIX | cytokeratin cocktail (m M3515, Dako) | + | no tumor, strongly positive in pneumocytes and bronchial epithelium |
|  |  | CD68 (m M814, Dako) | + | histiocytes |
| Spleen | Formalin | FVIII-related antigen (m M616, Dako) | + |  |
|  |  | CD45 (m M701, Dako) | + |  |
| Placenta | UM-FIX | human chorionic gonadotropin (p A231, Dako) | + |  |
|  |  | human placental lectin (p A137, Dako) | + |  |
|  |  | P57 (m MS1062-P, Lab Vision) | + |  |
|  |  | CD34 (m 347660 B-D) | + |  |
|  |  | Myeloperoxidase (p A324, Dako) | + |  |
| Small bowel | Formalin | chromogranin A (m M869, Dako) | + |  |
|  |  | RET oncoprotein (m NCL-RET, Vector) | + |  |
| Appendix | Formalin | serotonin (m M758, Dako) | + |  |
| Breast | Formalin | estrogen receptor (1D5) (m M7047, Dako) | + | fibrocystic disease-weak reaction |
|  |  | progesterone receptor (m M3569, Dako) | + | strongly positive |
| Kidney | UM-FIX | P63 (m M7247, Dako) | + | transitional cell carcinoma |
|  |  | cytokeratin 20 (m M7019, Dako) | − |  |
| Skin | UM-FIX | epithelial membrane antigen (m M613, Dako) | + | sebaceous glands |
|  |  | T-F antigen (m M0898, Dako) | + | sebaceous glands |
| Liver | Formalin | CD68 (m M814, Dako) | + | Kupffer cells |
|  |  | cytokeratin 7 (m M7018, Dako) | + | bile duct epithelium |
| Breast | Formalin | S100 protein (p Z311, Dako) | + | myoepithelial cells |
| Uterus | Formalin | desmin (m M760, Dako) | + | myometrium and vessel wall |
|  |  | progesterone receptor (m M3569, Dako) | + | myometrium |

Example 5

DNA Extraction from Processed Tissue Sections

Two six micron tissue sections are placed in a 1.5 ml microfuge tube, 800 µl xylene is added and mixed by vortexing, 400 µl absolute ethanol is added and mixed by vortexing, the tube is centrifuged for 5 minutes in a microfuge, and the supernatant is decanted. To the pellet, 800 µl absolute ethanol is added and mixed by vortexing.

The supernatant is decanted after centrifugation, then 100 µl of a detergent and proteinase K solution (1% NP40 or Triton X-100, 2.4 µl of 2.5 mg/ml proteinase K) is added to the pellet and incubated at 55° C. for one hour. Proteinase K is inactivated by incubation at 95° C. for 10 minutes. The supernatant containing DNA is collected after centrifugation in a microfuge for 5 minutes. This material is ready for PCR. It should be precipitated and/or extracted further if Southern blotting is planned. More sections would be required to obtain enough DNA for restriction analysis.

Example 6

RNA Extraction from Processed Tissue Sections

Ten sections (7 μm each) from a block of processed tissue were chopped using disposable blades. They were placed in 50 ml Falcon tubes, deparaffinized with 20 ml of xylene, and the remaining tissue was then washed twice with absolute alcohol for 30 minutes. The tissue was suspended at 0.5 gm/ml in a solution containing 4M guanidinium thiocyanate, 25 mM Na citrate pH 7.0, 0.5% N-laurylsarcosine, and 0.1 M of 2-mercaptoethanol. The solution was mixed by vortexing and DNA was sheared by passage through an 18 to 22 gauge syringe needle.

The RNA-containing solution was carefully layered on 2.8 ml of 5.7 M CsCl in several 5 ml centrifuge tubes (Sorvall), and RNA was sedimented by centrifugation in an SW55Ti rotor at 35,000 rpm and 18° C. for 14 hours in a Beckman L8-53 ultracentrifuge. The top fraction was carefully removed to leave an RNA pellet at the bottom of the tube. The pellet was resuspended with ribonuclease-free water, and the Eppendorf tube was spun at 14,000 rpm for 10 minutes. The supernatant containing RNA was saved and the ultraviolet (UV) absorbance was measured: an extinction coefficient of 1 $OD_{280}$/cm is estimated to be the equivalent of about 40 μg/ml RNA and the $OD_{260}/OD_{280}$ ratio should be between about 1.8 and about 2.0.

Pieces of liver from two mice were placed in UM-FIX for approximately two hours and then processed in accordance with Example 3. Tissue was processed for either 15 minutes or 30 minutes in each of two reactions. The 18S and 28S rRNA bands of were separated by denaturing gel electrophoresis (FIG. 2). RNA extracted from fresh mouse liver was used as the positive control (lane C). RNA was extracted from processed liver tissue of two mice (lanes 1 and 2 from the first mouse; lanes 3 and 4 from the second mouse). Lanes 1 and 3 were processed for 15 minutes in each reaction; lanes 2 and 4 were processed for 30 minutes in each reaction. The 18S and 28S rRNA bands were present in the expected ratio and degradation was not seen.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

I claim:

1. A method for tissue processing of one or more tissue specimens using only two different chemical compositions and an apparatus comprising:
    a microwave unit comprised of (i) a first reaction chamber with an interior geometry comprised of a whispering gallery to achieve uniform distribution of microwave energy and heating of the interior, (ii) a single non-aqueous admixture which is optionally contained within the first reaction chamber, (iii) a source of microwave energy which is transmitted into the first reaction chamber to heat the non-aqueous admixture, and (iv) an agitator within the first reaction chamber to promote chemical exchange between the non-aqueous admixture and the tissue specimen and
    a vacuum unit comprised of (i) a second reaction chamber, (ii) a single wax solution which is optionally contained within the second reaction chamber, (iii) a source of radiant energy which is transmitted into the second reaction chamber to heat the wax solution, and (iv) a vacuum pump connected to the second reaction chamber;
    the method comprising:
    (a) initially impregnating a tissue specimen with the single non-aqueous admixture comprised of (i) fixing, (ii) dehydrating, and (iii) clearing functions which is agitated and heated; and then
    (b) substantially impregnating the tissue specimen with the single wax solution which is heated and also under less than atmospheric pressure.

2. The tissue processing method of claim 1, wherein the tissue specimen is about 3 mm or less in thickness.

3. The tissue processing method of claim 1, wherein tissue specimens are manually processed.

4. The tissue processing method of claim 1, wherein tissue specimens are mechanically processed.

5. The tissue processing method of claim 1, wherein the tissue specimen is processed without using an aldehyde.

6. The tissue processing method of claim 1, wherein the tissue specimen is processed without using a xylene.

7. The tissue processing method of claim 1, wherein the tissue specimen has not been fixed prior to processing.

8. The tissue processing method of claim 1, wherein the tissue specimen has been fixed in formaldehyde prior to processing.

9. The tissue processing method of claim 1, wherein the tissue specimen has been preserved in methanol and polyethylene glycol (PEG) prior to processing.

10. The tissue processing method of claim 1, wherein the tissue specimen is substantially hardened by the non-aqueous admixture, radiation from the microwave unit, or both.

11. The tissue processing method of claim 1, wherein the non-aqueous admixture is above about 55° C. and/or below about 75° C.

12. The tissue processing method of claim 1, wherein the non-aqueous admixture is comprised of fixative and dehydrant in a volume ratio greater than about 1:6 and/or less than about 6:1.

13. The tissue processing method of claim 1, wherein a fixative is greater than about 20% (v/v) and/or less than about 60% (v/v) of the non-aqueous admixture.

14. The tissue processing method of claim 1, wherein a dehydrant is greater than about 20% (v/v) and/or less than about 60% (v/v) of the non-aqueous admixture.

15. The tissue processing method of claim 1, wherein a clearant is greater than about 10% (v/v) and/or less than about 30% (v/v) of the non-aqueous admixture.

16. The tissue processing method of claim 1, wherein the non-aqueous admixture is further comprised of a surfactant.

17. The tissue processing method of claim 1, wherein the non-aqueous admixture is comprised of a fixative which is at least one ketone and a dehydrant which is at least one alcohol.

18. The tissue processing method of claim 1, wherein the non-aqueous admixture is comprised of a clearant which is mineral oil.

19. The tissue processing method of claim 1, wherein the non-aqueous admixture is further comprised of dimethyl sulfoxide (DMSO).

20. The tissue processing method of claim 1, wherein the non-aqueous admixture is comprised of about 15% (v/v) to about 35% (v/v) acetone, about 45% (v/v) to about 65% (v/v) isopropyl alcohol, and about 10% (v/v) to about 25% (v/v) mineral oil.

21. The tissue processing method of claim 1, wherein the non-aqueous admixture is comprised of about 40% to about 60% (v/v) of acetone, about 25% to about 35% (v/v) of isopropanol, and about 10% (v/v) to about 25% (v/v) of mineral oil.

22. The tissue processing method of claim 1, wherein the tissue specimen is substantially hardened after being incubated in the non-aqueous admixture for about 15 minutes or less.

23. The tissue processing method of claim 1, wherein the tissue specimen is substantially hardened after being incubated in the non-aqueous admixture for about 30 minutes or less.

24. The tissue processing method of claim 1, wherein the tissue specimen is substantially hardened after being incubated in the non-aqueous admixture for about 45 minutes or less.

25. The tissue processing method of Claim 1, wherein the tissue specimen is substantially impregnated at a pressure above about 100 torr and/or below about 760 torr.

26. The tissue processing method of claim 1, wherein the wax solution is above about 55° C. and/or below about 85° C.

27. The tissue processing method of claim 1, wherein the wax solution has been degassed and dehydrated.

28. The tissue processing method of claim 1, wherein the wax solution is made from paraffin which is solid below about 30° C.

29. The tissue processing method of claim 1, wherein the tissue specimen can be sectioned after being incubated in the wax solution for about 15 minutes or less, and then cooled.

30. The tissue processing method of claim 1, wherein the tissue specimen can be sectioned after being incubated in the wax solution for about 30 minutes or less, and then cooled.

31. The tissue processing method of claim 1, wherein the tissue specimen can be sectioned after being incubated in the wax solution for about 45 minutes or less, and then cooled.

32. A method for tissue processing of one or more tissue specimens using only two different chemical compositions and an apparatus comprising:
   a first module comprising (i) a first reaction chamber with an interior geometry comprised of a whispering gallery to achieve uniform distribution of microwave energy and heating of the interior, (ii) a single non-aqueous admixture which is optionally contained within the first reaction chamber, (iii) a source of microwave energy which is transmitted into the first reaction chamber to heat the non-aqueous admixture, and (iv) an agitator within the first reaction chamber to promote chemical exchange between the non-aqueous admixture and the tissue specimen and
   a second module comprising (i) a second reaction chamber, (ii) a single wax solution which is optionally contained within the second reaction chamber, (iii) a source of radiant energy which is transmitted into the second reaction chamber to heat the wax solution, and (iv) a vacuum pump connected to the second reaction chamber;
   the method comprising:
   (a) initially impregnating a tissue specimen in the first module with the single non-aqueous admixture comprised of (i) at least one ketone, (ii) at least one alcohol, and (iii) mineral oil while being agitated and heated then
   (b) substantially impregnating the tissue specimen in the second module with the single wax solution while being under vacuum and heated.

33. The tissue processing method of claim 32, wherein tissue specimens are manually processed.

34. The tissue processing method of claim 32, wherein the tissue specimen is substantially hardened by the non-aqueous admixture, radiation from the microwave unit, or both.

35. The tissue processing method of claim 32, wherein the tissue specimen is substantially impregnated at a pressure above about 100 torr and/or below about 760 torr.

* * * * *